United States Patent [19]

Regel et al.

[11] Patent Number: 4,618,619

[45] Date of Patent: Oct. 21, 1986

[54] SUBSTITUTED T-BUTANOL FUNGICIDAL AGENTS

[75] Inventors: Erik Regel, Wuppertal; Karl H. Büchel, Burscheid; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 589,613

[22] Filed: Mar. 14, 1984

[30] Foreign Application Priority Data

Mar. 30, 1983 [DE] Fed. Rep. of Germany ....... 3311702

[51] Int. Cl.$^4$ ...................... A01N 43/50; A01N 43/64
[52] U.S. Cl. .................................. 514/383; 514/397; 514/399
[58] Field of Search ............... 424/269, 273 R, 273 P; 514/383

[56] References Cited

U.S. PATENT DOCUMENTS 4,416,682  11/1983  Worthington ..................... 548/336

FOREIGN PATENT DOCUMENTS

| 0040345 | 11/1981 | European Pat. Off. ............ 548/262 |
| 0044605 | 1/1982  | European Pat. Off. . |
| 0059894 | 9/1982  | European Pat. Off. ............ 548/262 |
| 0061835 | 10/1982 | European Pat. Off. ............ 548/262 |
| 2908378 | 9/1980  | Fed. Rep. of Germany ...... 548/262 |
| 2103210 | 2/1983  | United Kingdom ................ 424/269 |

Primary Examiner—Allen J. Robinson
Attorney, Agent, or Firm—Sprung Horn Kramer & Woods

[57] ABSTRACT

A method of combating plant pathogenic fungi which comprises administering to such fungi or to a habitat thereof a plant pathogenic fungicidally effective amount of a substituted tert.-butanol derivative of the formula

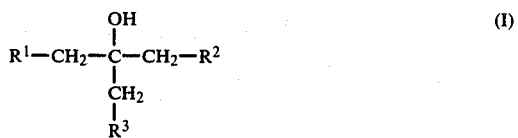

in which $R^1$, $R^2$ and $R^3$ are identical or different and represent azolyl, optionally substituted phenoxy, optionally substituted phenylthio, alkylthio, alkenyl, alkinyl, optionally substituted phenylacetylenyl, alkylamino, dialkylamino, optionally substituted phenylamino, optionally substituted phenyl-N-alkylamino, optionally substituted cycloalkylamino, optionally substituted cycloalkyl-N-alkyl-amino, aminoethoxy, alkylaminoethoxy or dialkylaminoethyoxy, or an acid addition salt or metal salt complex thereof.

9 Claims, No Drawings

SUBSTITUTED T-BUTANOL FUNGICIDAL AGENTS

The present invention relates to the use of substituted tert.-butanol derivatives, which have not yet been described, as fungicidal agents.

It has already been disclosed that certain diazolyl derivatives, such as, for example, 2-(4-chlorophenyl)- or -(2-chlorophenyl)-1,3-di(1,2,4-triazol-1-yl)-2-propanol and 2-(4-chlorophenyl)-1,3-di(imidazol-1-yl)-2-propanol, have good fungicidal properties (compare EP-OS (European Published Specification) 0,044,605). However, the action of these compounds is not always completely satisfactory, especially when low amounts and concentrations are applied.

It has been found that the substituted tert.-butanol derivatives of the general formula

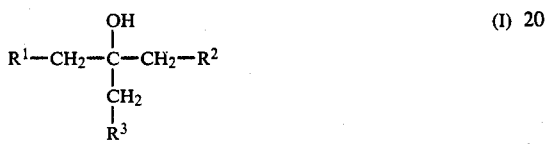

in which $R^1$, $R^2$ and $R^3$ are identical or different and represent azolyl, optionally substituted phenoxy, optionally substituted phenylthio, alkylthio, alkenyl, alkinyl, optionally substituted phenylacetylenyl, alkylamino, dialkylamino, optionally substituted phenylamino, optionally substituted phenyl-N-alkyl-amino, optionally substituted cycloalkylamino, optionally substituted cycloalkyl-N-alkyl-amino, aminoethoxy, alkylaminoethoxy or dialkylaminoethoxy, and acid addition salts and metal salt complexes thereof have good fungicidal properties.

Surprisingly, the substituted tert.-butanol derivatives of the formula (I) to be used according to the invention have a better fungicidal activity than the diazolyl-derivatives 2-(4-chlorophenyl)- or -(2-chlorophenyl)-1,3-di(1,2,4-triazol-1-yl)-2-propanol and 2-(4-chlorophenyl)-1,3-di(imidazol-1-yl)-2-propanol, which are already known from the prior art and are closely related compounds structurally and from the point of view of their action. The use, according to the invention, of the new substances thus represents an enrichment of the art.

Formula (I) provides a general definition of the substituted tert.-butanol derivatives to be used according to the invention.

Preferred compounds of the formula (I) are those in which (A)
$R^1$ and $R^2$ are identical or different and represent imidazol-1-yl, 1,2,4-triazol-1-yl; 1,2,4-triazol-4-yl or pyrazol-1-yl and $R^3$ represents phenoxy, phenylthio, phenylamino or phenyl-N-alkyl-amino with 1 to 4 carbon atoms in the alkyl part, each of which is optionally monosubstituted or polysubstituted by identical or different substituents, possible substituents on the phenyl in each case being: halogen, alkyl with 1 to 6 carbon atoms, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms, cycloalkyl with 5 to 6 carbon atoms; nitro, cyano, hydroxycarbonyl, alkylcarbonyl or alkoxycarbonyl with in each case 1 to 4 carbon atoms in the alkyl part, phenyl or phenoxy which is optionally monosubstituted or polysubstituted by identical or different substituents from the group comprising halogen, nitro, trifluoromethyl and alkyl with 1 or 2 carbon atoms, the aldehyde group or the oxime or oxime ether radical.

Preferred compounds of the general formula (I) are also those in which (B)
$R^1$ and $R^2$ are identical or different and represent imidazol-1-yl, 1,2,4-triazol-1-yl, 1,2,4-triazol-4-yl or pyrazol-1-yl and $R^3$ represents alkylthio with 1 to 12 carbon atoms, alkylamino or dialkylamino with in each case 1 to 4 carbon atoms in each alkyl part, aminoethoxy, alkylaminoethoxy and dialkylaminoethoxy with in each case 1 to 4 carbon atoms in each alkyl part, or cycloalkylamino or cycloalkyl-N-alkylamino with in each case 3 to 7 carbon atoms in the cycloalkyl part and 1 to 4 carbon atoms in the alkyl part and in each case optionally monosubstituted or polysubstituted by identical or different substituents in the cycloalkyl part, possible substituents being: halogen, alkyl with 1 to 4 carbon atoms and alkoxy with 1 or 2 carbon atoms.

Preferred compounds of the formula (I) are furthermore those in which (C)
$R^1$ represents imidazol-1-yl; 1,2,4-triazol-1-yl; 1,2,4-triazol-4-yl or pyrazol-1-yl and $R^2$ and $R^3$ are identical or different and represent the substituents mentioned for $R^3$ under point (A).

Preferred compounds of the formula (I) are moreover those in which (D)
$R^1$ represents imidazol-1-yl; 1,2,4-triazol-1-yl; 1,2,4-triazol-4-yl or pyrazol-1-yl and $R^2$ and $R^3$ are identical or different and represent the meanings for $R^3$ given above under point (B).

Preferred compounds of the formula (I) are likewise those in which (E)
$R^1$, $R^2$ and $R^3$ are identical or different and represent the meanings for $R^3$ mentioned above under points (A) and (B).

Finally, preferred compounds of the formula (I) are also those in which (F)
$R^1$, $R^2$ and $R^3$ are identical or different and represent the meanings for $R^1$ mentioned above under point (A).

Particularly preferred compounds of the formula (I) are those in which (A)
$R^1$ and $R^2$ are identical or different and represent imidazol-1-yl; 1,2,4-triazol-1-yl; 1,2,4-triazol-4-yl or pyrazol-1-yl and $R^3$ represents phenoxy, phenylthio, phenylamino or phenyl-N-alkyl-amino with 1 or 2 carbon atoms in the alkyl part, each of which is optionally mono-, di- or tri-substituted by identical or different substituents, possible substituents on the phenyl in each case being: fluorine, chlorine, bromine, methyl, ethyl, isopropyl, tert.-butyl, 2-methyl-but-2-yl, methoxy, ethoxy, methylthio, trifluoromethyl, trifluoromethoxy, trifluoromethylthio, cyclohexyl, nitro, cyano, hydroxycarbonyl, methylcarbonyl, methoxycarbonyl or ethoxycarbonyl, or phenyl or phenoxy, each of which is optionally mono-, di- or tri-substituted by identical or different substituents from the group comprising chlorine, nitro, trifluoromethyl and methyl, or the aldehyde group, hydroxyiminomethyl or methoxyiminomethyl.

Particularly preferred compounds of the formula (I) are also those in which (B)

R$^1$ and R$^2$ are identical or different and represent imidazol-1-yl; 1,2,4-triazol-1-yl; 1,2,4-triazol-4-yl or pyrazol-1-yl and R$^3$ represents methylthio, ethylthio, butylthio or dodecylthio, or alkylamino or dialkylamino with in each case 1 or 2 carbon atoms in each alkyl part, or aminoethoxy, alkylaminoethoxy or dialkylaminoethoxy with in each case 1 or 2 carbon atoms in each alkyl part, or cyclopropylamino, cyclopentylamino, cyclohexylamino, cyclopropyl-N-methyl-amino, cyclopentyl-N-methyl-amino or cyclohexyl-N-methyl-amino, each of which is optionally mono-, di- or tri-substituted in the cycloalkyl part by identical or different substituents, possible substituents being: chlorine, bromine, methyl, ethyl, isopropyl and methoxy.

Particularly preferred compounds of the formula (I) are furthermore those in which (C)

R$^1$ represents imidazol-1-yl; 1,2,4-triazol-1-yl; 1,2,4-triazol-4-yl or pyrazol-1-yl and R$^2$ and R$^3$ are identical or different and have the meanings for R$^3$ mentioned above under point (A).

Particularly preferred compounds of the formula (I) are moreover those in which (D)

R$^1$ represents imidazol-1-yl; 1,2,4-triazol-1-yl; 1,2,4-triazol-4-yl or pyrazol-1-yl and R$^2$ and R$^3$ are identical or different and represent the meanings for R$^3$ mentioned above under point (B).

Particularly preferred compounds of the formula (I) are likewise those in which (E)

R$^1$, R$^2$ and R$^3$ are identical or different and represent the meanings for R$^3$ mentioned above under points (A) and (B).

Finally, particularly preferred compounds of the formula (I) are also those in which (F)

R$^1$, R$^2$ and R$^3$ are identical or different and represent the meanings for R$^1$ mentioned above under point (A).

Addition products of acids and those substituted tert.-butanol derivatives of the formula (I) in which the substituents R$^1$, R$^2$ and R$^3$ have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulfonic acid and 1,5-naphthalenedisulphonic acid.

Addition products of salts of metals of main groups II to IV and of sub-groups I and II and IV to VIII and those substituted tert.-butanol derivatives of the formula (I) in which the substituents R$^1$, R$^2$ and R$^3$ have the meanings which have already been mentioned as preferred for these substituents are also preferred compounds according to the invention.

The salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and sal peracid and sulphuric acid.

The following compounds of the general formula (I) may be mentioned specifically, in addition to the compounds mentioned in the preparation examples:

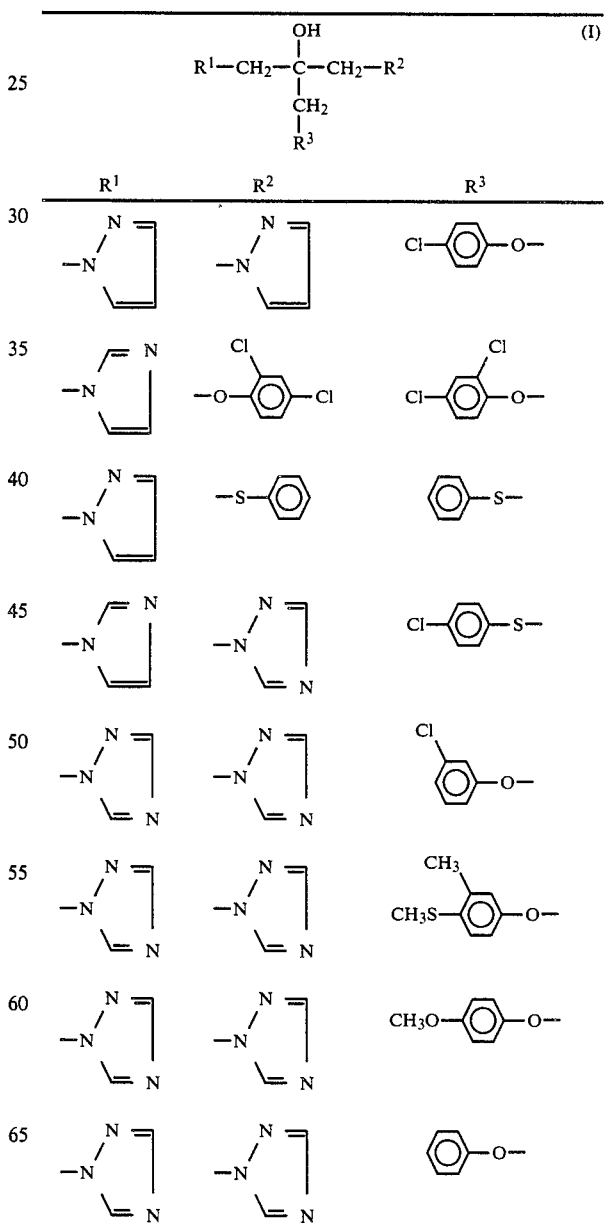

-continued $$R^1-CH_2-\underset{\underset{R^3}{\overset{|}{CH_2}}}{\overset{\overset{OH}{|}}{C}}-CH_2-R^2 \quad (I)$$

| $R^1$ | $R^2$ | $R^3$ |
|---|---|---|
| ![1,2,4-triazol-1-yl] | ![1,2,4-triazol-1-yl] | 3,4-dichlorophenoxy |
| ![1,2,4-triazol-1-yl] | ![1,2,4-triazol-1-yl] | $(C_2H_5)_2N-CH_2CH_2-O-$ |
| ![1,2,4-triazol-1-yl] | ![1,2,4-triazol-1-yl] | 4-phenylphenylthio |
| ![1,2,4-triazol-1-yl] | ![1,2,4-triazol-1-yl] | 2,4,5-trichlorophenoxy |
| ![1,2,4-triazol-1-yl] | ![1,2,4-triazol-1-yl] | 2,3,5-trichlorophenoxy |
| ![1,2,4-triazol-1-yl] | ![1,2,4-triazol-1-yl] | 4-bromophenoxy |
| ![1,2,4-triazol-1-yl] | ![1,2,4-triazol-1-yl] | 2,6-dichlorophenylamino |

The active compounds to be used according to the invention are not yet known. However, they are the subject of Application Ser. No. 522,428, filed Aug. 11, 1983, now pending, (German patent application P 32 32 647 [Le A 21 916] of 2.9.1982), and are obtained by reacting a nucleophile of the formula $$R^1-H \quad (II)$$

in which
$R^1$ has the abovementioned meaning,
(a) with 2,2-dihalogenomethyloxiranes of the formula $$\underset{O}{\overset{CH_2}{\diagdown}}\underset{}{\overset{}{\diagup}}C\underset{CH_2Hal}{\overset{CH_2Hal}{\diagdown}} \quad (III)$$

in which Hal represents halogen,
in the presence of an inert organic solvent, such as, for example, acetone, and in the presence of an acid-binding agent, such as, for example, potassium carbonate, at temperatures between 20° and 120° C., or
(b) with 2-halogenomethyloxiranes of the formula $$\underset{O}{\overset{CH_2}{\diagdown}}\underset{}{\overset{}{\diagup}}C\underset{CH_2-Hal}{\overset{CH_2-R^2}{\diagdown}} \quad (IV)$$

in which $R^2$ and Hal have the abovementioned meaning, in the presence of an inert organic solvent, such as, for example, acetone, and in the presence of an acid-binding agent, such as, for example, potassium carbonate, at temperatures between 20° and 120° C., or
(c) with substituted oxiranes of the formula $$\underset{O}{\overset{CH_2}{\diagdown}}\underset{}{\overset{}{\diagup}}C\underset{CH_2-R^3}{\overset{CH_2-R^2}{\diagdown}} \quad (V)$$

in which $R^2$ and $R^3$ have the abovementioned meaning, in the presence of an inert organic solvent, such as, for example, acetone, and in the presence of an acid-binding agent, such as, for example, potassium carbonate, at temperatures between 20° and 120° C.

The nucleophiles of the formula (II) are generally known compounds of organic chemistry.

2,2-dihalogenomethyloxiranes of the formula (III) are known (compare Beilstein, E III (1), pages 1587–1588), and can be obtained in a known manner, in which 3-halogeno-2-halogenomethylpropenes of the formula $$CH_2=C\underset{CH_2Hal}{\overset{CH_2Hal}{\diagdown}} \quad (VI)$$

in which Hal has the abovementioned meaning,
either are first reacted with tert.-butyloxy halide to give 1,3-dihalogeno-2-halogenomethyl-2-propanols of the formula $$Hal-CH_2-\underset{\underset{Hal}{\overset{|}{CH_2}}}{\overset{\overset{OH}{|}}{C}}-CH_2-Hal \quad (VII)$$

in which Hal has the abovementioned meaning,
and these are then epoxidized in the presence of calcium hydroxide to give the desired 2,2-dihalogenomethyloxiranes of the formula (III) (in this context, compare also Beilstein, E III (1), pages 1587–1588); or are epoxidized directly in the presence of peracids, such as, for example, peracetic acid or m-chloroperbenzoic acid, to give the desired 2,2-dihalogenomethyloxiranes of the formula (III).

The 2-halogenomethyloxiranes of the formula (IV) are not yet known. However, they can be obtained in the generally customary manner, by either reacting 2,2-dihalogenomethyloxiranes of the formula (III) with a nucleophile of the formula (II); or first reacting 3-halogeno-2-halogenomethyl-propenes of the formula (VI) with a nucleophile of the formula (II), if necessary in the form of an alkyl metal salt, to give propenes of the formula

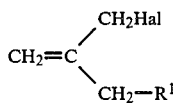 (VIII)

in which Hal and $R^1$ have the abovementioned meaning, and then epoxidizing these compounds in the presence of peracids to give the desired 2-halogenomethyloxiranes of the formula (IV).

The substituted oxiranes of the formula (V) are not yet known. However, they can be obtained in the generally customary manner by either reacting 2,2-dihalogenomethyloxiranes of the formula (III) with a nucleophile of the formula (II); or reacting 3-halogeno-2-halogenomethyl-propenes of the formula (VI) with a nucleophile of the formula (LI), if necessary in the form of an alkali metal salt, to give the propenes of the formula

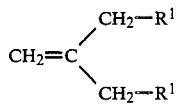 (IX)

in which $R^1$ has the abovementioned meaning,
and then epoxidizing these compounds in the presence of peracids to give the desired oxiranes of the formula (V); or epoxidizing ketones of the formula

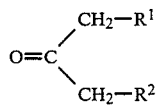 (X)

in which $R^1$ and $R^2$ have the abovementioned meaning, with dimethylsulphonium methylide in a manner which is known per se.

Certain compounds of the formula (I) can also be obtained by reacting di(halogenomethyl)-carbinols of the formula (XI)

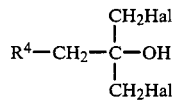 (XI)

in which
Hal has the abovementioned meaning and
$R^1$ represents optionally substituted phenylthio, alkylthio, alkylamino, dialkylamino, optionally substituted phenylamino, optionally substituted phenyl-N-alkylamino, optionally substituted cycloalkylamino or optionally substituted cycloalkyl-N-alkyl-amino,
under the conditions of process (a).

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as *Erysiphe graminis, Leptosphaeria nodorum,* Puccinia sp., *Cochliobolus sativus* and *Pyrenophora teres;* Sphaerotheca species, such as *Sphaerotheca fuliginea,* and rice diseases, such as Pyricularia and Pellicularia. Moreover, the active compounds according to the invention display a broad in vitro fungicidal action spectrum.

When applied in appropriate amounts, the compounds according to the invention also exhibit a plant growth-regulating action.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1 and 2

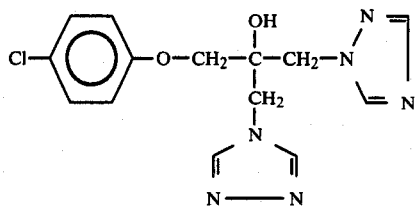
(Example 1)

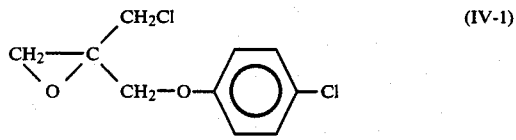
(Example 2)

(Process b)

9.4 g (0.04 mole) of 2-chloromethyl-2-(4-chlorophenoxymethyl)-oxirane are added dropwise to a mixture of 13.6 g (0.2 mole) of 1,2,4-triazole and 13.8 g (0.1 mole) of potassium carbonate in 200 ml of acetone, while stirring. The reaction mixture is stirred at room tempereture for 15 hours and then under reflux for 22 hours. It is then filtered cold and the filtrate is concentrated in vacuo. The oily residue is dissolved in chloroform and the solution is washed with water, dried over sodium sulphate and purified by chromatography (silica gel 60 Merck, chloroform/methanol=20/1). 5.8 g (43% of theory) of 2-(4-chlorophenoxymethyl)-1,3-di(1,2,4-triazol-1-yl)-2-hydroxypropane of melting point 99° C. (Example 1) and 2.0 g (15% of theory) of 2-(4-chlorophenoxymethyl)-2-hydroxy-1-(1,2,4-triazol-1-yl)-3-(1,2,4-triazol-4-yl)-propane (Example 2) of melting point 160° C. are obtained.

Preparation of the starting substance

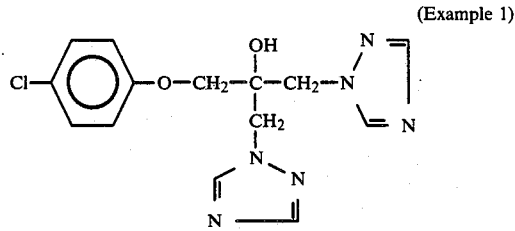
(IV-1)

(1st variant)

12.85 g (0.1 mole) of 4-chlorophenol in 50 ml of acetone are added dropwise to a mixture of 14.1 g (0.1 mole) of 2,2-di(chloromethyl)-oxirane and 13.8 g (0.1 mole) of potassium carbonate in 200 ml of acetone. The mixture is heated under reflux for 18 hours and allowed to cool and is filtered. The filtrate is concentrated in vacuo, the residue is dissolved in chloroform and the solution is washed with water, dried over sodium sulphate and concentrated. After purification by distillation, 7.6 g (32.5% of theory) of 2-chloromethyl-2-(4-chlorophenoxymethyl)-oxirane of boiling point 150° C./0.5 mbar are obtained.

(2nd variant)

0.5 mole of sodium 4-chlorophenolate in acetonitrile is added dropwise to a solution of 125 g (1 mole) of 3-chloro-2-chloromethylpropane in 50 ml of acetonitrile. After addition of 0.5 g of sodium iodide, the reaction mixture is heated under reflux for 12 hours and then filtered cold. The filtrate is concentrated in vacuo. The residue is dissolved in methylene chloride and the solution is washed with water, dried over sodium sulphate and concentrated. 58.6 g of approximately 60% pure 2-chloromethyl-3r(4-chlorophenoxy)propene are obtained, and are dissolved in 500 ml of methylene chloride. 43 g (0.25 mole) of 3-chloroperbenzoic acid are added.

The mixture is stirred at room temperature for 24 hours and filtered. The filtrate is washed with aqueous, 10% strength sodium thiosulphate solution, dried over sodium sulphate and concentrated in vacuo.

After purification by distillation, 30 g (12.9% of theory) of 2-chloromethyl-2-(4-chlorophenoxymethyl)oxirane of refractive index $n_D^{20}$ 1.5465 are obtained.

Example 3, 4 and 5

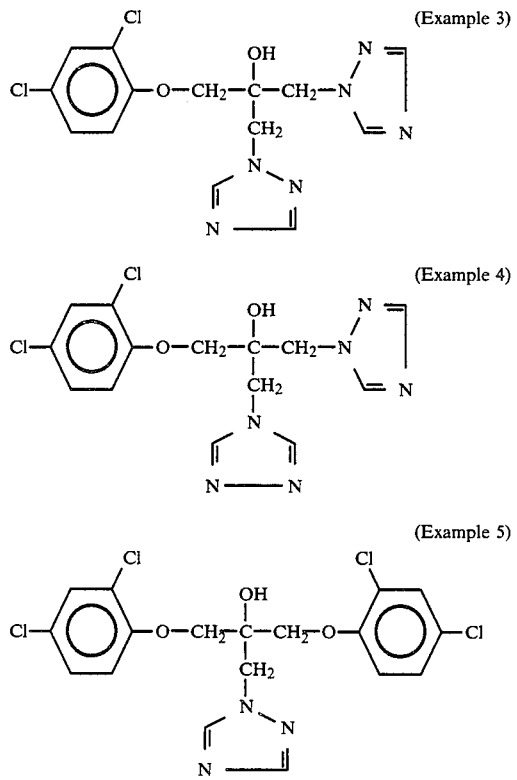

(Processes b and c)

23.5 g of a mixture of 2-chloromethyl-2-(2,4-dichlorophenoxymethyl)-oxirane and 2,2-bis(2,4-dichlorophenoxymethyl)-oxirane are added dropwise to a solution of 20.7 g (0.3 mole) of 1,2,4-triazole and 13.8 g (0.1 mole) of potassium carbonate in 200 ml of acetone. The reaction mixture is stirred under reflux for 20 hours. It is then filtered cold and the filtrate is concentrated in vacuo. The residue is dissolved in chloroform and the solution is washed with water, dried over sodium sulphate and purified and separated by chromatography (silica gel 60 Merck). Chloroform is first used as the eluting agent. The eluate thereby obtained is concentrated by distilling off the solvent and the residue is stirred with diethyl ether. 4.8 g of 1,3-bis-(2,4-dichlorophenoxy)-2-hydroxy-2-(1,2,4-triazol-1-yl-methyl)-propane (Example 5) of melting point 136° C. are obtained.

Chloroform/methanol: 40/1 is then used as the eluting agent. The eluate thereby obtained is concentrated by distilling off the solvent and the residue is stirred with acetonitrile. 3.9 g of 2-(2,4-dichlorophenoxymethyl)-1,3-di(1,2,4-triazol-1-yl)-2-hydroxypropane (Example 3) of melting point 138° C. are obtained.

Finally, chloroform/methanol: 20/1 is used as the eluting agent. The eluate thereby obtained is concentrated by distilling off the solvent and the residue is stirred with acetonitrile. 3.7 g of 2-(2,4-dichlorophenoxymethyl)-2-hydroxy-1-(1,2,4-triazol-1-yl)-3-(1,2,4-triazol-4-yl)-propane (Example 4) of melting point 182° C. are obtained.

Preparation of the starting substances

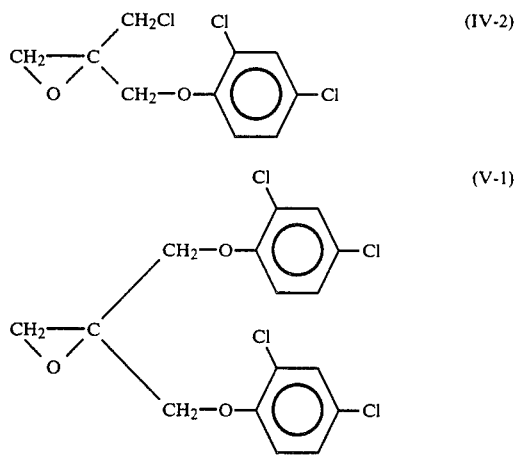

A mixture of 14.1 g (0.1 mole) of 2,2-di(chloromethyl)-oxirane, 13.8 g (0.1 mole) of potassium carbonate and 16.3 g (0.1 mole) of 2,4-dichlorophenol in 150 ml of acetone is heated at 60° C. for 15 hours and then filtered cold and the filtrate is concentrated in vacuo. The residue is taken up in methylene chloride and the mixture is washed with water, dried over sodium sulphate and concentrated. 23.5 g of an oily mixture which, on the basis of determination by gas chromatography, contains 47% of 2-chloromethyl-2-(2,4-dichlorophenoxymethyl)oxirane (Example IV-2) and 24.9% of 2,2-bis(2,4-dichlorophenoxymethyl)-oxirane (Example V-1), in addition to 14.9% of unreacted 2,2-di(chloromethyl)-oxirane, are obtained.

If desired, this mixture can be separated into its components by chromatography, 2-chloromethyl-2-(2,4-dichlorophenoxymethyl)-oxirane (Example IV-2) of refractive index $n_D^{20}$ 1.5568 and 2,2-bis(2,4-dichlorophenoxymethyl)-oxirane (Example V-1) of melting point 64° C. being obtained.

Example 6

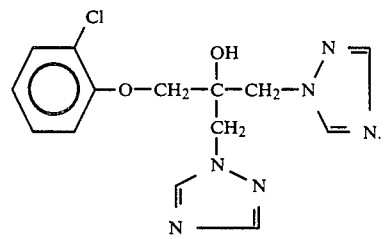

(Process b)

7.1 g (55% of theory) of 2-(2-chlorophenoxymethyl)-1,3-di(1,2,4-triazol-1-yl)-2-hydroxy-propane of melting point 95° C. are obtained according to Example 1/2 from 8.9 g (0.038 mole) of 2-chloromethyl-2-(2-chlorophenoxymethyl)-oxirane, 5 g (0.038 mole) of potassium carbonate and 6.9 g (0.1 mole) of 1,2,4-triazole in 200 ml of acetone, after purification of the reaction product by chromatography (silica gel 60, Merck, chloroform/methanol=40/1).

Preparation of the starting substance

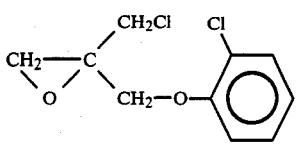
(IV-3)

9.1 g (39% of theory) of 2-chloromethyl-2-(2-chlorophenoxymethyl)-oxirane of refractive index $n_D^{20}$ 1.5463 are obtained according to Example 1/2 (preparation of the starting substance, 1st variant) from 12.85 g (0.1 mole) of 2-chlorophenol in 50 ml of acetone and 14.1 g (0.1 mole) of 2,2-di(chloromethyl)-oxirane as well as 13.8 g (0.1 mole) of potassium carbonate in 200 ml of acetone.

Example 7

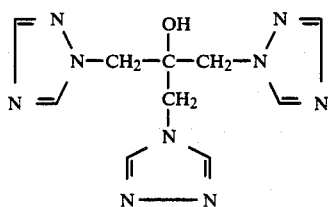

(Process a)

28.2 g (0.2 mole) of 2,2-di(chloromethyl)-oxirane are added dropwise to a mixture of 82.5 g (1.2 moles) of 1,2,4-triazole and 82.5 g (0.6 mole) of potassium carbonate in 400 ml of acetone, while stirring. The reaction mixture is stirred under reflux for 50 hours and filtered and the filtrate is concentrated in vacuo. The oily residue is chromatographed (silica gel 60, Merck, chloroform/methanol=20/1). 5.9 g (10.7% of theory) of 1,3-di(1,2,4-triazol-1-yl)-2-hydroxy-2-(1,2,4-triazol-4-yl-methyl)-propane of melting point 220° C. are obtained.

Example 8 and 9

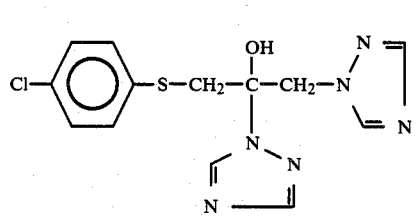
(Example 8)

-continued
(Example 9)

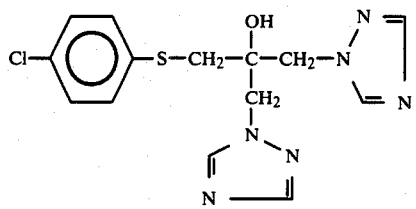

(Process b)

12.1 g (57.5% of theory) of 2-(4-chlorophenylthiomethyl)-1,3-di(1,2,4-triazol-1-yl)-2-hydroxy-propane (Example 8) of melting point 150° C. and 4.6 g (22% of theory) of 2-(4-chlorophenylthiomethyl)-2-hydroxy-1-(1,2,4-triazol-1-yl)-3-(1,2,4-triazol-4-yl)-propane (Example 9) of melting point 186° C. are obtained according to Example 1/2 from 14.8 g (0.06 mole) of 2-chloromethyl-2-(4-chlorophenylthiomethyl)-oxirane, 8.3 g (0.12 mole) of 1,2,4-triazole and 8.3 g (0.06 mole) of potassium carbonate in 200 ml of acetone.

Preparation of the starting substance

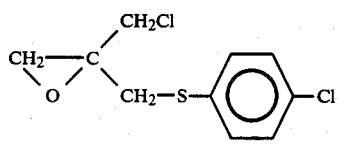
(IV-4)

5.4 g (0.1 mole) of sodium methylate are introduced in portions into a mixture of 16.9 g (0.12 mole) of 2,2-di(chloromethyl)-oxirane and 14.5 g (0.1 mole) of 4-chlorothiophenol in 200 ml of acetonitrile. The reaction mixture is subsequently stirred for 4 hours and filtered and the filtrate is concentrated in vacuo. The residue is dissolved in methylene chloride and the solution is washed with water, dried over sodium sulphate and concentrated. The oil which remains is distilled. 18.2 g (73% of theory) of 2-chloromethyl-2-(4-chlorophenylthiomethyl)-oxirane of refractive index $n_D^{20}$ 1.5895 are obtained.

The following end products of the general formula $$R^1-CH_2-\underset{\underset{R^3}{\overset{CH_2}{|}}}{\overset{OH}{\underset{|}{C}}}-CH_2-R^2 \quad (I)$$

in Table 1 are obtained in a corresponding manner and by the processes according to the invention:

TABLE 1

| Example No. | $R^1$ | $R^2$ | $R^3$ | Melting point (°C.) or $n_D^{20}$ |
|---|---|---|---|---|
| 10 | 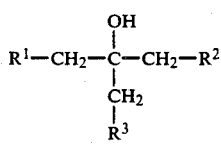 | (triazolyl) | (2,6-dichlorophenoxy) | 166 |

TABLE 1-continued

| Example No. | R¹ | R² | R³ | Melting point (°C.) or $n_D^{20}$ |
|---|---|---|---|---|
| 11 | " | " | —O—C₆H₄—F (4-fluorophenoxy) | 90 |
| 12 | " | " | —O—C₆H₄—C₆H₅ (4-phenylphenoxy) | 140 |
| 13 | " | " | —O—C₆H₄—CHO (4-formylphenoxy) | 179 |
| 14 | " | " | —O—C₆H₃(Cl)₂ (2,5-dichlorophenoxy) | 130 |
| 15 | " | 1,2,4-triazol-1-yl | —O—C₆H₄—Cl (2-chlorophenoxy) | 146 |
| 16 | " | " | —O—C₆H₃(Cl)₂ (2,6-dichlorophenoxy) | 150 |
| 17 | " | " | —O—C₆H₄—C₆H₅ (4-phenylphenoxy) | 204 |
| 18 | " | " | —O—C₆H₃(Cl)₂ (2,5-dichlorophenoxy) | 166 |
| 19 | " | —O—C₆H₄—Cl | —O—C₆H₄—Cl | 120 |
| 20 | 1,2,4-triazol-1-yl | —O—C₆H₄—Cl | —O—C₆H₄—Cl | 130 |
| 21 | —O—C₆H₄—Cl | —O—C₆H₄—Cl | —O—C₆H₄—Cl | 77 |

TABLE 1-continued

| Example No. | R¹ | R² | R³ | Melting point (°C.) or $n_D^{20}$ |
|---|---|---|---|---|
| 22 | —S—C₆H₄—Cl (4-) | —S—C₆H₄—Cl (4-) | —S—C₆H₄—Cl (4-) | 95 |
| 23 | 1,2,4-triazol-1-yl | 1,2,4-triazol-1-yl | —O—C₆H₄—Cl (3-) | 92 |
| 24 | 1,2,4-triazol-1-yl | 1,2,4-triazol-1-yl | —O—C₆H₄—Cl (3-) | 130 |
| 25 | imidazol-1-yl | imidazol-1-yl | —O—C₆H₄—Cl (4-) | 100 |
| 26 | 1,2,4-triazol-1-yl | —O—C₆H₄—Cl (4-) | —S—C₆H₄—Cl (4-) | 108 |
| 27 | pyrazol-1-yl | pyrazol-1-yl | —O—C₆H₄—Cl (4-) | 72 |
| 28 | 1,2,4-triazol-1-yl | 1,2,4-triazol-1-yl | —O—C₆H₅ | 84 |
| 29 | 1,2,4-triazol-1-yl | 1,2,4-triazol-1-yl | —O—C₆H₃—Cl₂ (3,4-) | 158 |
| 30 | " | 1,2,4-triazol-1-yl | —O—C₆H₅ | 112 |
| 31 | " | 1,2,4-triazol-1-yl | —O—C₆H₄—OCH₃ (4-) | 118 |
| 32 | " | 1,2,4-triazol-4-yl | —O—C₆H₄—OCH₃ (4-) | 162 |
| 33 | " | " | —O—C₆H₃—Cl₂ (3,4-) | 188 |

TABLE 1-continued

| Example No. | R¹ | R² | R³ | Melting point (°C.) or $n_D^{20}$ |
|---|---|---|---|---|
| 34 | " | —N(triazole) | —N(C₂H₅)—C₆H₅ | 110 |
| 35 | " | " | —O—C₆H₃(2-CH₃)(4-SCH₃) | 70 |
| 36 | " | —N(imidazole-like, N=N) | —O—C₆H₃(2-CH₃)(4-SCH₃) | 138 |
| 37 | " | —N(triazole) | —O—C₆H₃(2,4-Cl₂) | 162 |
| 38 | " | —N(triazole) | —O—C₆H₃(2,5-Cl₂) | 174 |
| 39 | " | —N(triazole) | —S—C₆H₃(2,4-(CH₃)₂) | 134 |
| 40 | " | —N(triazole) | —N(C₂H₅)—C₆H₅ | 84 |
| 41 | " | —N(triazole) | —O—C₆H₄—CH=N—OCH₃ | 120 |
| 42 | " | " | —O—C₆H₄—O—C₆H₄—Cl | 74 |
| 43 | " | —N(triazole) | —S—C₆H₃(2,4-(CH₃)₂) | 95 |
| 44 | " | —N(triazole) | —S—C₆H₃(2-CH₃)(4-OC₂H₅) | 75 |

TABLE 1-continued

| Example No. | $R^1$ | $R^2$ | $R^3$ | Melting point (°C.) or $n_D^{20}$ |
|---|---|---|---|---|
| 45 | " | 1,2,4-triazol-1-yl | —S—(2-CH₃-4-OC₂H₅-C₆H₃) | 93 |
| 46 | " | 1,2,4-triazol-1-yl | —S—C₂H₅ | 46 |
| 47 | " | " | —S—(4-Cl-C₆H₄) | 75 |
| 48 | " | " | —S—C₆H₅ | 70 |
| 49 | " | 1,2,4-triazol-1-yl | —S—C₆H₅ | 90 |
| 50 | " | 1,2,4-triazol-1-yl | —NH—(4-Cl-C₆H₄) | 116 |
| 51 | " | —NH—(4-Cl-C₆H₄) | —NH—(4-Cl-C₆H₄) | 128 |
| 52 | " | 1,2,4-triazol-1-yl | —S—(4-Br-C₆H₄) | 142 |
| 53 | " | 1,2,4-triazol-1-yl | —S—(4-Br-C₆H₄) | 186 |
| 54 | " | 1,2,4-triazol-1-yl | —S—(3,4-Cl₂-C₆H₃) | 149 |
| 55 | " | 1,2,4-triazol-1-yl | —S—(3,4-Cl₂-C₆H₃) | 155 |
| 56 | " | 1,2,4-triazol-1-yl | —S—(2-OCH₃-C₆H₄) | 1.5820 |

TABLE 1-continued

| Example No. | R¹ | R² | R³ | Melting point (°C.) or $n_D^{20}$ |
|---|---|---|---|---|
| 57 | " | -N(triazole) | -S-C₆H₄-OCH₃ | 45 |
| 58 | " | -N(triazole) | -NH-C₆H₃(Cl)₂ (2,4-diCl) | 130 |
| 59 | " | -N(triazole) | -NH-C₆H₃(Cl)₂ (2,4-diCl) | 150 |
| 60 | " | -N(triazole) | -NH-C₆H₃(Cl)₂ (3,4-diCl) | 126 |
| 61 | " | -N(triazole) | -NH-C₆H₃(Cl)₂ (3,4-diCl) | 95 |
| 62 | " | -NH-C₆H₃(Cl)₂ (3,4-diCl) | -NH-C₆H₃(Cl)₂ (3,4-diCl) | 170 |
| 63 | " | -N(triazole) | -N(CH₃)-C₆H₄-Cl | 142 |
| 64 | " | -N(triazole) | -N(CH₃)-C₆H₄-Cl | 177 |
| 65 | " | -N(triazole) | -S-C₆H₃(Cl)₂ (2,4-diCl) | 90 |
| 66 | " | -N(triazole) | -S-C₆H₃(Cl)₂ (2,4-diCl) | 70 |
| 67 | " | -N(triazole) | -NH-C₆H₃(CH₃)₂ (2,6-diMe) | 1.5620 |

TABLE 1-continued

| Example No. | R¹ | R² | R³ | Melting point (°C.) or $n_D^{20}$ |
|---|---|---|---|---|
| 68 | " | -N(N=CH-N=CH) (1,2,4-triazol-1-yl) | -NH-C₆H₄-Cl (3-chloro) | 1.5698 |
| 69 | " | " | -S-C₆H₄-C(CH₃)(CH₃)C₂H₅ (para) | 1.5600 |
| 70 | " | " | -S-C₆H₄-OCH₃ (ortho) | 80 |
| 71 | " | -N(N=CH-N=CH) (1,2,4-triazol-4-yl) | -S-C₆H₄-OCH₃ (ortho) | 108 |
| 72 | " | -N(N=CH-N=CH) (1,2,4-triazol-1-yl) | -S-C₆H₄-C(CH₃)₃ (para) | 1.5608 |
| 73 | " | " | -S-C₆H₃(OCH₃)(OCH₃) (2,4-dimethoxy) | 126 |
| 74 | " | -N(N=CH-N=CH) (1,2,4-triazol-4-yl) | -S-C₆H₄-C(CH₃)(CH₃)C₂H₅ (para) | 142 |
| 75 | " | " | -S-C₆H₄-C(CH₃)₃ (para) | 144 |
| 76 | " | " | -S-C₆H₃(OCH₃)(OCH₃) (2,4-dimethoxy) | viscous oil |
| 77 | " | -N(N=CH-N=CH) (1,2,4-triazol-1-yl) | -NH-C₆H₃(Cl)(Cl) (2,5-dichloro) | 168 |
| 78 | " | -N(N=CH-N=CH) (1,2,4-triazol-1-yl) | -N(N=CH-N=CH) (1,2,4-triazol-1-yl) | 146 |

TABLE 1-continued
| Example No. | R¹ | R² | R³ | Melting point (°C.) or $n_D^{20}$ |
|---|---|---|---|---|
| 79 | " | 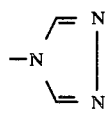 | 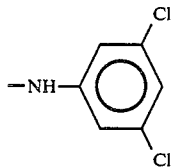 | 108 |
| 80 | " | 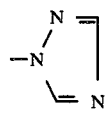 | 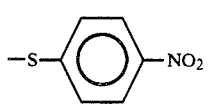 | 150 |
| 81 | " | 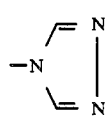 | 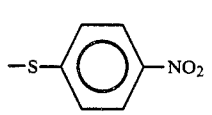 | 188 |
| 82 | " | 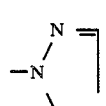 | 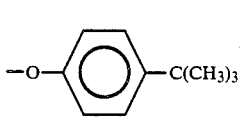 | 98 |
| 83 | " | 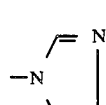 | 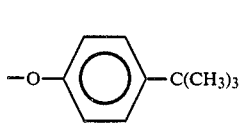 | 164 |
| 84 | " | 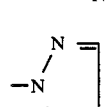 | 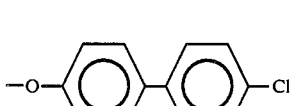 | 166 |
| 85 | " | 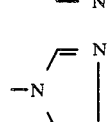 | 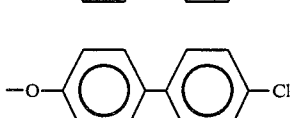 | 194 |
| 86 | " | 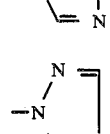 |  | 128 |
| 87 | " | 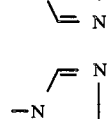 | 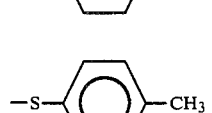 | 141 |
| 88 | " | 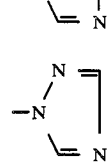 | 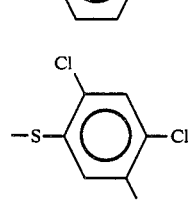 | 115 |
| 89 | " | 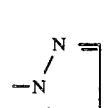 | 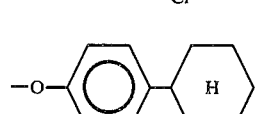 | 96 |
| 90 | " | 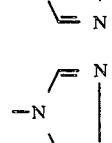 | 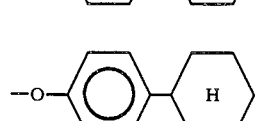 | 159 |

TABLE 1-continued
| Example No. | R¹ | R² | R³ | Melting point (°C.) or $n_D^{20}$ |
|---|---|---|---|---|
| 91 | " | 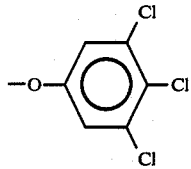 | 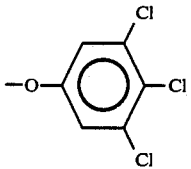 | 160 |
| 92 | " | 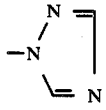 | 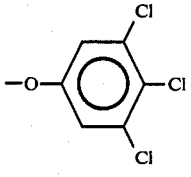 | 184 |
| 93 | " | 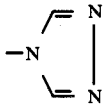 | 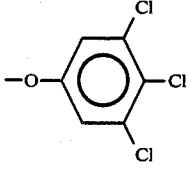 | 186 |
| 94 | " | 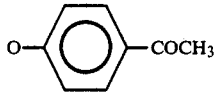 | 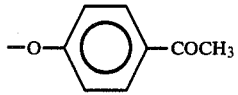 | 1.5750 |
| 95 | " | 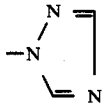 | 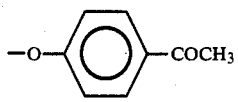 | 142 |
| 96 | " | 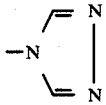 | 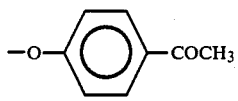 | 190 |
| 97 | " | 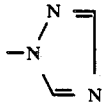 | 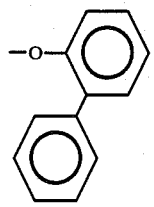 | 120 |
| 98 | " | 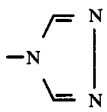 | 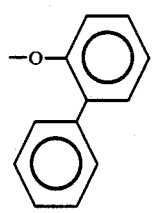 | 130 |
| 99 | " | 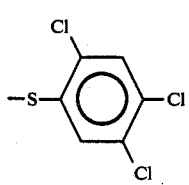 | 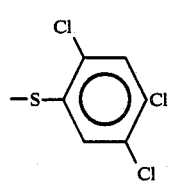 | 154 |

TABLE 1-continued

| Example No. | R¹ | R² | R³ | Melting point (°C.) or $n_D^{20}$ |
|---|---|---|---|---|
| 100 | " | -N(1,2,4-triazol-4-yl) | -S-(2,4,5-trichlorophenyl) | 80 |
| 101 | " | -N(1,2,4-triazol-1-yl) | -S-(4-fluorophenyl) | 114 |
| 102 | " | -N(1,2,4-triazol-4-yl) | -S-(4-fluorophenyl) | 169 |
| 103 | " | -N(1,2,4-triazol-1-yl) | -O-C₆H₄-C(=NOCH₃)CH₃ | 140 |
| 104 | " | -N(1,2,4-triazol-4-yl) | -O-C₆H₄-C(=NOCH₃)CH₃ | 154 |
| 105 | " | -N(1,2,4-triazol-1-yl) | -S-(3-CF₃-4-Cl-phenyl) | 50 |
| 106 | " | -N(1,2,4-triazol-4-yl) | -S-(3-CF₃-4-Cl-phenyl) | 75 |
| 107 | " | -N(1,2,4-triazol-1-yl) | $-S-(CH_2)_{11}-CH_3$ | 70 |
| 108 | -N(1,2,4-triazol-1-yl) | -O-(2,4-dichlorophenyl) | -O-(2,4-dichlorophenyl) | 169 |
| 109 | " | $-S-(CH_2)_{11}-CH_3$ | $-S-(CH_2)_{11}-CH_3$ | 84 |
| 110 | " | -N(1,2,4-triazol-1-yl) | $-S-(CH_2)_{11}-CH_3$ | 82 |
| 111 | -N(1,2,4-triazol-4-yl) | $-S-(CH_2)_{11}-CH_3$ | $-S-(CH_2)_{11}-CH_3$ | 51 |

TABLE 1-continued
| Example No. | R¹ | R² | R³ | Melting point (°C.) or $n_D^{20}$ |
|---|---|---|---|---|
| 112 | " | 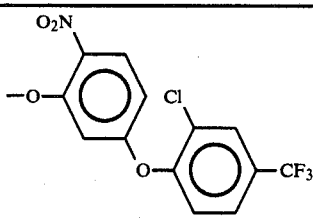 | 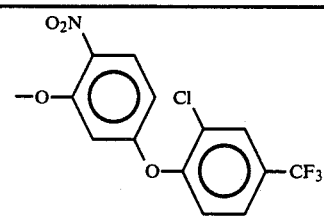 | 96 |
| 113 | " | 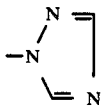 | 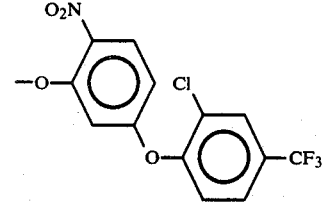 | 92 |
| 114 | " | 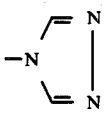 | 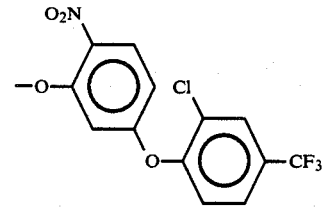 | 130 |
| 115 | " | 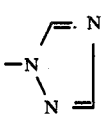 | $-S-C(CH_3)_3$ | 70 |
| 116 | " | 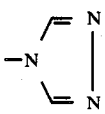 | $-S-C(CH_3)_3$ | 91 |
| 117 | " | 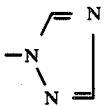 | 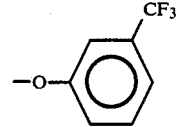 | 97 |
| 118 | " | 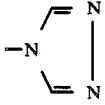 | 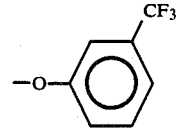 | 110 |
| 119 | " | 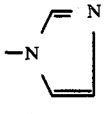 | 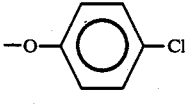 | 100 |
| 120 | 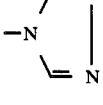 | 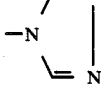 | 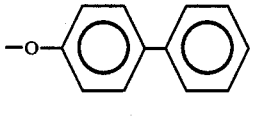 | 275 |
| 121 | 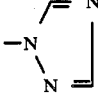 | 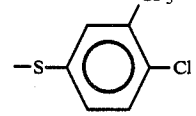 | 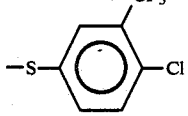 | 1.5674 |

The following intermediates of the general formula (IV)

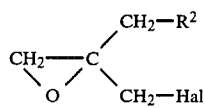

in Table 2 are obtained according to the preparation examples and the general statements on the process:

TABLE 2

| Example No. | R² | Hal | Boiling point (°C.) or $n_D^{20}$ |
|---|---|---|---|
| (IV-5) | —O—C₆H₄—F (4-F) | Cl | 100/0.2 |
| (IV-6) | —O—C₆H₃(Cl)₂ (2,4-diCl) | Cl | 145/0.1 |
| (IV-7) | —O—C₆H₃(Cl)₂ (2,6-diCl) | Cl | 155/0.3 |
| (IV-8) | —O—C₆H₄—C₆H₅ | Cl | 1.5842 |
| (IV-9) | —O—C₆H₄—CHO | Cl | 190/0.2 |
| (IV-10) | —N(C₂H₅)—C₆H₁₁ | Cl | 100/0.1 |
| (IV-11) | —S—C₆H₃(NO₂)(Cl) | Cl | 1.6270 |
| (IV-12) | —O—C₆H₄—O—C₆H₄—Cl | Cl | 1.5442 |
| (IV-13) | —O—C₆H₄—Cl | Cl | 140/0.5 |
| (IV-14) | —S—C₆H₃(CH₃)₂ | Cl | 122/0.1 |
| (IV-15) | —O—C₆H₅ | Cl | 110/0.1 |
| (IV-16) | —O—C₆H₄—OCH₃ | Cl | 120/0.2 |
| (IV-17) | —O—C₆H₃(Cl)₂ | Cl | 140/0.2 |
| (IV-18) | —O—C₆H₃(Cl)₂ | Cl | 140/0.2 |
| (IV-19) | —O—C₆H₃(CH₃)(SCH₃) | Cl | 160/0.2 |
| (IV-20) | —S—C₆H₅ | Cl | 120/0.3 |
| (IV-21) | —S—C₆H₃(CH₃)(OC₂H₅) | Cl | 138/0.1 |
| (IV-22) | —S—C₂H₅ | Cl | 1.4968 |
| (IV-23) | —N(C₂H₅)—C₆H₅ | Cl | 130/0.3 |
| (IV-24) | —NH—C₆H₄—Cl | Cl | 1.5843 |
| (IV-25) | —S—C₆H₄—OCH₃ | Cl | 160/0.3 |
| (IV-26) | —S—C₆H₄—Br | Cl | 158/0.3 |
| (IV-27) | —S—C₆H₃(Cl)₂ | Cl | 155/0.3 |
| (IV-28) | —S—C₆H₄—CH₃ | Cl | 1.5575 |
| (IV-29) | —S—(CH₂)₁₁—CH₃ | Cl | 1.4775 |
| (IV-30) | —S—C₆H₂(Cl)₃ | Cl | 1.6065 |
| (IV-31) | —S—C₆H₃(Cl)₂ | Cl | 1.5951 |
| (IV-32) | —S—C₆H₄—C(CH₃)₃ | Cl | 1.5514 |
| (IV-33) | —S—C₆H₄—C(CH₃)₂C₂H₅ | Cl | 1.5408 |
| (IV-34) | —S—C₆H₄—OCH₃ | Cl | 1.5748 |

TABLE 2-continued

| Example No. | R² | Hal | Boiling point (°C.) or n_D^20 |
|---|---|---|---|
| (IV-35) | CH₃O—S—⌬—OCH₃ | Cl | 1.5613 |
| (IV-36) | CH₃—N(CH₃)—⌬—Cl | Cl | 1.5738 |
| (IV-37) | —NH—⌬(Cl)(Cl) | Cl | 1.5805 |
| (IV-38) | —NH—⌬(Cl)(Cl) | Cl | 1.5858 |
| (IV-39) | —NH—⌬(Cl)(Cl) | Cl | 1.5940 |
| (IV-40) | —S—⌬—COOH | Cl | 1.5840 |
| (IV-41) | NO₂—O—⌬—O—⌬(Cl)(CF₃) | Cl | 1.5531 |
| (IV-42) | —SC(CH₃)₃ | Cl | 1.4871 |
| (IV-43) | —O—⌬—CF₃ | Cl | 1.4880 |

The following intermediates of the general formula (V)

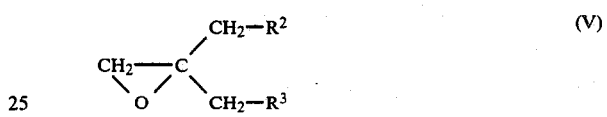

in Table 3 are obtained according to the preparation examples and the general statements of the process:

TABLE 3

| Example No. | R² | R³ | Melting point (°C.) or n_D^20 |
|---|---|---|---|
| (V-2) | —O—⌬—Cl | —S—⌬—Cl | 1.6347 |
| (V-3) | —O—⌬—Cl | —O—⌬—Cl | 84 |
| (V-4) | —O—⌬—⌬ | —O—⌬—⌬ | 176 |
| (V-5) | —O—⌬ | —O—⌬ | 1.5612 |
| (V-6) | —O—⌬—OCH₃ | —O—⌬—OCH₃ | 100 |
| (V-7) | —O—⌬—Cl | —N(triazole) | 1.5590 |
| (V-8) | —O—⌬—O—⌬—Cl | —O—⌬—O—⌬—Cl | 50 |

| Example No. | R² | R³ | Melting point (°C.) or $n_D^{20}$ |
|---|---|---|---|
| (V-9) | 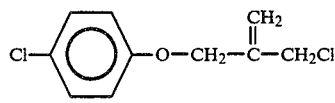 | 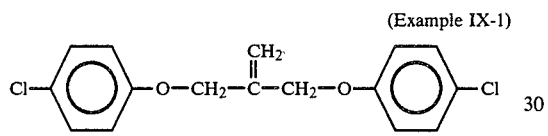 | 96 |

The preparation of the propene derivatives of the formulae (VIII) and (IX) to be used, if appropriate, as intermediates may be illustrated with the aid of the following examples:

Example α

(Example VIII-1)

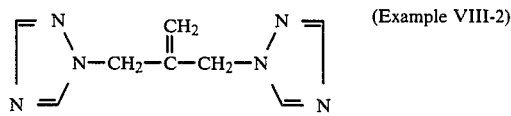

(Example IX-1)

A solution of 64.25 g (0.5 mole) of 4-chlorophenol in 100 ml of acetone is added dropwise to a mixture of 125 g (1 mole) of 3-chloro-2-chloromethyl-propene and 34.5 g (0.25 mole) of potassium carbonate in 500 ml of acetone at 60° C. The mixture is subsequently stirred at this temperature for 18 hours and filtered and the filtrate is concentrated. The oily residue is dissolved in methylene chloride and the solution is washed once with 200 ml of 10% strength sodium hydroxide solution and then twice with in each case 500 ml of water, dried over sodium sulphate and concentrated. The oily residue is distilled. 43.2 g (41.5% of theory) of 2-chloromethyl-3-(4-chlorophenoxy)-propene (Example VIII-1) of boiling point 80° to 90° C./0.05 mbar are obtained.

10.7 g of 3-(4-chlorophenoxy)-2-(4-chlorophenoxymethyl)-propene (Example IX-1) of melting point 72° C. are obtained from the distillation residue after stirring with diisopropyl ether.

Example β

(Example VIII-2)

A mixture of 25 g (0.2 mole) of 3-chloro-2-chloromethyl-propene, 27.6 g (0.4 mole) of 1,2,4-triazole and 27.6 g (0.2 mole) of potassium carbonate in 200 ml of acetone is heated under reflux for 15 hours. After cooling, the mixture is filtered and the filtrate is concentrated in vacuo. The oily residue is chromatographed (silica gel 60, Merck; chloroform).

23 g (63% of theory) of 3-(1,2,4-triazol-1-yl)-2-(1,2,4-triazol-1-yl-methyl)-propene of melting point 52° C. are obtained.

Use Examples

The compounds shown below are used as comparison substances in the examples which follow:

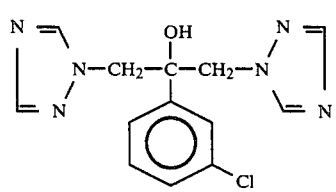 (A)

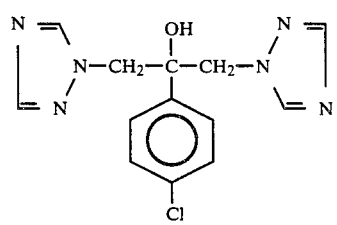 (B)

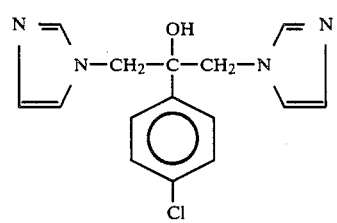 (C)

Example A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 3, 5, 8, 11, 14, 23, 29, 31, 60, 65, 88 and 92.

TABLE A

Erysiphe Test (barley)/protective

| Active compound | Active compound concentration in the spray liquor in % by weight | Disease infestation in % of the untreated control |
| --- | --- | --- |
| (A) (known) 3-chlorophenyl bis-triazolyl carbinol structure | 0.0025 | 100 |
| (5) bis(2,4-dichlorophenoxymethyl) triazolyl carbinol | 0.0025 | 33.7 |
| (3) 2,4-dichlorophenoxy bis-triazolyl structure | 0.0025 | 0.0 |
| (11) 4-fluorophenoxy bis-triazolyl structure | 0.0025 | 25.0 |
| (14) 2,5-dichlorophenoxy bis-triazolyl structure | 0.0025 | 25.0 |
| (23) 3-chlorophenoxy bis-triazolyl structure | 0.0025 | 12.5 |
| (31) 4-methoxyphenoxy bis-triazolyl structure | 0.0025 | 16.2 |

TABLE A-continued

Erysiphe Test (barley)/protective

| Active compound | Active compound concentration in the spray liquor in % by weight | Disease infestation in % of the untreated control |
|---|---|---|
| (8) 4-Cl-C$_6$H$_4$-S-CH$_2$-C(OH)(CH$_2$-triazolyl)-CH$_2$-triazolyl | 0.0025 | 25.0 |
| (29) 3,4-Cl$_2$-C$_6$H$_3$-O-CH$_2$-C(OH)(CH$_2$-triazolyl)-CH$_2$-triazolyl | 0.0025 | 25.0 |
| (60) 3,4-Cl$_2$-C$_6$H$_3$-NH-CH$_2$-C(OH)(CH$_2$-triazolyl)-CH$_2$-triazolyl | 0.0025 | 16.2 |
| (65) 2,4-Cl$_2$-C$_6$H$_3$-S-CH$_2$-C(OH)(CH$_2$-triazolyl)-CH$_2$-triazolyl | 0.0025 | 3.7 |
| (88) 2,4,5-Cl$_3$-C$_6$H$_2$-S-CH$_2$-C(OH)(CH$_2$-triazolyl)-CH$_2$-triazolyl | 0.0025 | 12.5 |
| (92) 2,4,5-Cl$_3$-C$_6$H$_2$-O-CH$_2$-C(OH)(CH$_2$-triazolyl)-CH$_2$-triazolyl | 0.0025 | 25.0 |

Example B

*Leptosphaeria nodorum* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compound according to the following preparation example: 5.

TABLE B

*Leptosphaeria nodorum* test (wheat)/protective

| Active compound | Active compound concentration in the spray liquor in % by weight | Disease infestation in % of the untreated control |
|---|---|---|
| 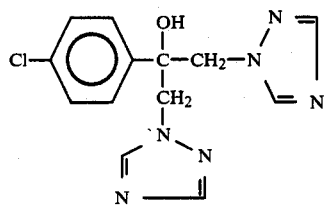 (B) (known) | 0.025 | 100 |
| 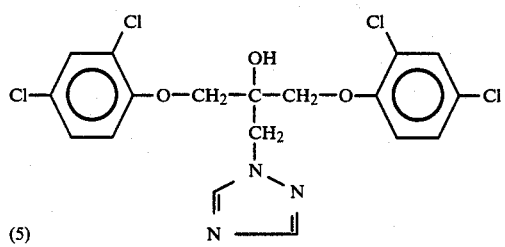 (5) | 0.025 | 33.3 |

Example C

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 6, 3, 8, 12 and 29.

TABLE C

Sphaerotheca test (cucumber)/protective

| Active compound | Infestation in % at an active compound concentration of 100 |
|---|---|
| 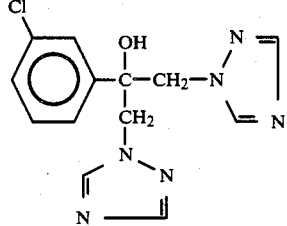 (C) (known) | |
| 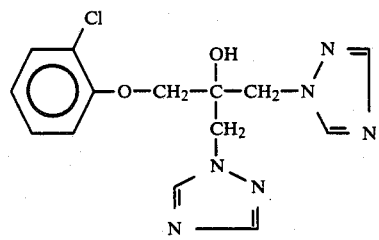 (A) (known) | 43 |
| (6) | 10 |

TABLE C-continued

Sphaerotheca test (cucumber)/protective

| Active compound | Infestation in % at an active compound concentration of |
|---|---|
| 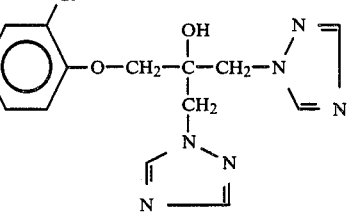 (3) | 10 |
| 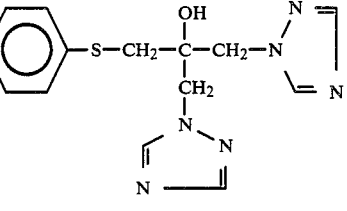 (8) | 20 |
| 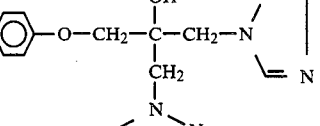 (12) | 30 |

TABLE C-continued

Sphaerotheca test (cucumber)/protective

| Active compound | Infestation in % at an active compound concentration of |
|---|---|
|  (29) | 13 |

Example D

Cochliobolus sativus test (barley)/protective
Solvent: 100 parts by weight of dimethylformaide
Emulsifier: 0.25 parts by weight of alkyl aryl polyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 12, 52, 54, 69, 72, 82, 86, 89, 91, 94, 95, 96, 97, 98, 99, 100, 101, 103.

TABLE D

Cochliobolus sativus test (barley)/protective

| Active compound | Active compound concentration in the spray liquor in % by weight | Disease infestation in % of the untreated control |
|---|---|---|
| (B) (known) | 0.025 | 100 |

TABLE D-continued

Cochliobolus sativus test (barley)/protective

| Active compound | Active compound concentration in the spray liquor in % by weight | Disease infestation in % of the untreated control |
| --- | --- | --- |
| (12) biphenyl-O-CH₂-C(OH)(CH₂-triazolyl)(CH₂-triazolyl) | 0.025 | 16.2 |
| (52) 4-Br-C₆H₄-S-CH₂-C(OH)(CH₂-triazolyl)(CH₂-triazolyl) | 0.025 | 0.0 |
| (54) 3,4-Cl₂-C₆H₃-S-CH₂-C(OH)(CH₂-triazolyl)(CH₂-triazolyl) | 0.025 | 0.0 |
| (69) 4-(2-methylbut-2-yl)-C₆H₄-S-CH₂-C(OH)(CH₂-triazolyl)(CH₂-triazolyl) | 0.025 | 12.5 |
| (72) 4-(CH₃)₃C-C₆H₄-S-CH₂-C(OH)(CH₂-triazolyl)(CH₂-triazolyl) | 0.025 | 12.5 |
| (82) 4-(CH₃)₃C-C₆H₄-O-CH₂-C(OH)(CH₂-triazolyl)(CH₂-triazolyl) | 0.025 | 50.0 |

TABLE D-continued

Cochliobolus sativus test (barley)/protective

| Active compound | Active compound concentration in the spray liquor in % by weight | Disease infestation in % of the untreated control |
| --- | --- | --- |
| (86) 4-methylphenyl-S-CH₂-C(OH)(CH₂-triazolyl)-CH₂-triazolyl | 0.025 | 12.5 |
| (89) 4-cyclohexylphenyl-O-CH₂-C(OH)(CH₂-triazolyl)-CH₂-triazolyl | 0.025 | 25.0 |
| (91) bis(3,4,5-trichlorophenoxy)-CH₂-C(OH)(CH₂-triazolyl)-CH₂ | 0.025 | 50.0 |
| (94) bis(4-acetylphenoxy)-CH₂-C(OH)(CH₂-triazolyl)-CH₂ | 0.025 | 50.0 |
| (95) 4-acetylphenyl-O-CH₂-C(OH)(CH₂-triazolyl)-CH₂-triazolyl | 0.025 | 50.0 |
| (96) 4-acetylphenyl-O-CH₂-C(OH)(CH₂-triazolyl)-CH₂-triazolyl | 0.025 | 50.0 |

TABLE D-continued

*Cochliobolus sativus* test (barley)/protective

| Active compound | Active compound concentration in the spray liquor in % by weight | Disease infestation in % of the untreated control |
|---|---|---|
| (97) biphenyl-O-CH₂-C(OH)(CH₂-triazole)(CH₂-triazole) | 0.025 | 50.0 |
| (98) biphenyl-O-CH₂-C(OH)(CH₂-triazole)(CH₂-triazole) | 0.025 | 25.0 |
| (99) (2,4,5-trichlorophenyl)-S-CH₂-C(OH)(CH₂-S-(2,4,5-trichlorophenyl))(CH₂-triazole) | 0.025 | 25.0 |
| (100) (2,4,5-trichlorophenyl)-S-CH₂-C(OH)(CH₂-triazole)(CH₂-triazole) | 0.025 | 33.7 |
| (101) (4-fluorophenyl)-S-CH₂-C(OH)(CH₂-triazole)(CH₂-triazole) | 0.025 | 50.0 |

TABLE D-continued

*Cochliobolus sativus* test (barley)/protective

| Active compound | Active compound concentration in the spray liquor in % by weight | Disease infestation in % of the untreated control |
|---|---|---|
| 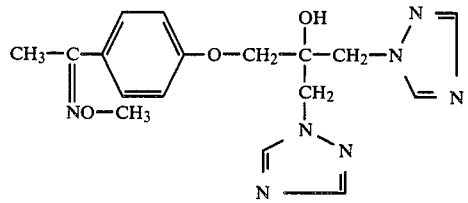 (103) | 0.025 | 50.0 |

It will be appreciated that the instant specification and examples are set forth by way of illustration and not limitation, and that various modifications and changes may be made without departing from the spirit and scope of the present invention.

What is claimed is:

1. A method of combating plant pathogenic fungi comprises administering to such fungi or to a habitat thereof a plant pathogenic fungicidally effective amount of a substituted tert.-butanol derivative of the formula

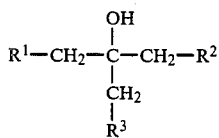

in which
R$^1$ and R$^2$ each independently is selected from the group consisting of 1,2,4-triazol-1-yl and 1,2,4-triazol-4-yl, and
R$^3$ is a member selected from the group consisting of phenoxy; phenoxy substituted up to three times by at least one substituent independently selected from the group consisting of fluorine, chlorine, bromine, methyl, tert.-butyl, methoxy, methylthio, trifluoromethyl, cyclohexyl, nitro, methylcarbonyl, phenyl, chlorophenyl, phenoxy, chlorophenoxy, the radical of the formula

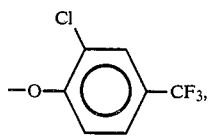

methoximinomethyl, the radical of the formula CH$_3$

and the —CHO group; phenylthio; and phenylthio substituted up to three times by at least one substituent independently selected from the group consisting of fluorine, chlorine, bromine, methyl, tert.-butyl, 2-methyl-but-2-yl, methoxy, ethoxy, trifluoromethyl and nitro.

2. The method according to claim 1, wherein such compound is 2-(2,4-dichlorophenoxymethyl)-1,3-di(1,2,4-triazol-1-yl)-2-hydroxypropane of the formula

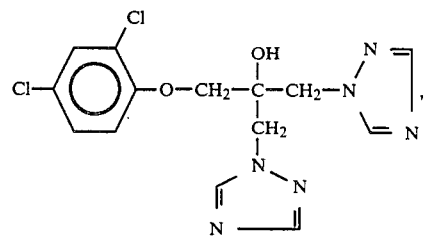

an acid addition salt or metal salt complex thereof.

3. The method according to claim 1, wherein such compound is 2-(2-chlorophenoxymethyl)-1,3-di(1,2,4-triazol-1-yl)-2-hydroxypropane of the formula

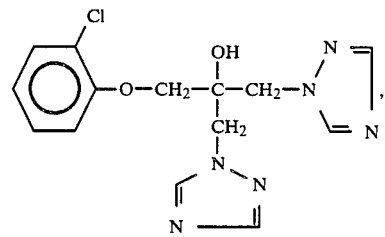

an acid addition salt or metal salt complex thereof.

4. The method according to claim 1, wherein such compound is 2-(4-biphenylyloxymethyl)-1,3-di(1,2,4-triazol-1-yl)-2-hydroxypropane of the formula

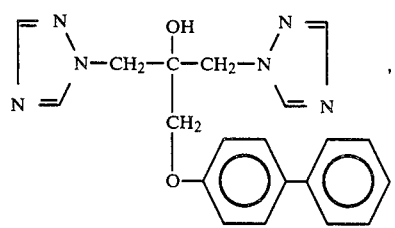

an acid addition salt or metal salt complex thereof.

5. The method according to claim 1, wherein such compound is 2-(3,4-dichlorophenoxymethy)-1,3-di(1,2,4-triazol-1-yl)-2-hydroxypropane of the formula

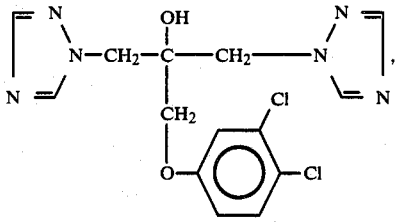

an acid addition salt or metal salt complex thereof.

6. The method according to claim 1, wherein such compound is 2-(4-bromophenylthiomethyl)-1,3-di(1,2,4-triazol-1-yl)-2-hydroxypropane of the formula

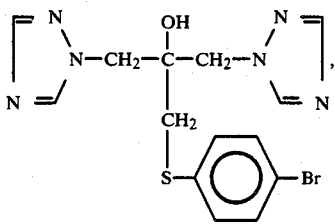

an acid addition salt or metal salt complex thereof.

7. The method according to claim 1, wherein such compound is 2-(3,4-dichlorophenylthiomethyl)-1,3-di(1,2,4-triazol-1-yl)-2-hydroxypropane of the formula

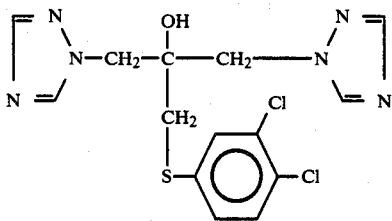

an acid addition or metal salt complex thereof.

8. A method according to claim 1, wherein $R^1$ and $R^2$ are identical.

9. A method according to claim 1, wherein for $R^3$, said halogen atoms are selected from the group consisting of fluorine and chlorine.

* * * * *

UNITED STATES PATENT AND TRADEMARK OFFICE
CERTIFICATE OF CORRECTION

PATENT NO. : 4,618,619
DATED : October 21, 1986
INVENTOR(S) : Erik Regel, et al.

It is certified that error appears in the above-identified patent and that said Letters Patent are hereby corrected as shown below:

| | |
|---|---|
| Title Page, Abstract, line 15 | Correct spelling of --dialkylaminoethoxy-- |
| Col. 7, line 1 | Delete "alkyl" and substitute --alkyli-- |
| Col. 10, line 56 | Delete "chloromethylpropane" and substitute --chloromethylpropene-- |
| Col. 53, Compound No. 98 | Delete end of formula and substitute |

Col. 55, lines 55-60   Delete formula and substitute $$-\underset{|}{\overset{CH_3}{C}}=NOCH_3 \quad --$$

Signed and Sealed this

Fifteenth Day of September, 1987

Attest:

DONALD J. QUIGG

Attesting Officer   Commissioner of Patents and Trademarks